(12) United States Patent
Orbay et al.

(10) Patent No.: US 7,699,880 B2
(45) Date of Patent: Apr. 20, 2010

(54) BONE FIXATION SYSTEM AND BONE SCREWS HAVING ANTI-BACK OUT FEATURE

(75) Inventors: Jorge L. Orbay, Miami, FL (US);
Javier E. Castañeda, Miami, FL (US);
Cesare Cavallazzi, Miramar, FL (US)

(73) Assignee: DePuy Products, Inc., Warsaw, IN (US)

( * ) Notice: Subject to any disclaimer, the term of this patent is extended or adjusted under 35 U.S.C. 154(b) by 1079 days.

(21) Appl. No.: 11/257,177

(22) Filed: Oct. 24, 2005

(65) Prior Publication Data

US 2007/0118125 A1    May 24, 2007

(51) Int. Cl.
*A61B 17/58* (2006.01)
*A61B 17/80* (2006.01)

(52) U.S. Cl. ...................... 606/290; 606/294
(58) Field of Classification Search ................. 606/294, 606/290, 293, 303, 319, 308; 411/125, 127, 411/128, 326, 961, 962
See application file for complete search history.

(56) References Cited

U.S. PATENT DOCUMENTS

| | | | | |
|---|---|---|---|---|
| 32,880 A | * | 7/1861 | Lawrence et al. | 411/114 |
| 1,427,313 A | * | 8/1922 | Morse | 411/324 |
| 1,714,711 A | * | 5/1929 | Elkin | 411/133 |
| 3,419,057 A | * | 12/1968 | Hogan | 411/125 |
| 3,779,240 A | * | 12/1973 | Kondo | 606/282 |
| 4,763,456 A | * | 8/1988 | Giannuzzi | 52/410 |
| 5,275,601 A | * | 1/1994 | Gogolewski et al. | 606/291 |
| 5,578,034 A | | 11/1996 | Estes | |
| 5,606,753 A | * | 3/1997 | Hashimoto | 411/7 |
| 5,967,721 A | * | 10/1999 | Giachinta et al. | 411/7 |
| 5,997,538 A | * | 12/1999 | Asnis et al. | 606/916 |
| 6,227,782 B1 | * | 5/2001 | Bowling et al. | 411/114 |
| 6,258,089 B1 | | 7/2001 | Campbell et al. | |
| 6,261,291 B1 | | 7/2001 | Talaber et al. | |
| 6,264,411 B1 | * | 7/2001 | DiStasio et al. | 411/329 |
| 6,302,883 B1 | * | 10/2001 | Bono | 606/291 |
| 6,361,537 B1 | * | 3/2002 | Anderson | 606/86 B |
| 2001/0041894 A1 | | 11/2001 | Campbell et al. | 606/61 |
| 2005/0049593 A1 | * | 3/2005 | Duong et al. | 606/69 |
| 2005/0096657 A1 | * | 5/2005 | Autericque et al. | 606/69 |
| 2006/0155285 A1 | * | 7/2006 | Anderson | 606/70 |

FOREIGN PATENT DOCUMENTS

| | | |
|---|---|---|
| CA | 2449883 | 5/2005 |
| DE | 10243791 | 3/2004 |
| DE | 4409833 | 10/2005 |
| WO | WO 9525474 A1 * | 9/1995 |

* cited by examiner

*Primary Examiner*—Thomas C Barrett
*Assistant Examiner*—Sameh Boles
(74) *Attorney, Agent, or Firm*—Gordon & Jacobson, PC

(57) ABSTRACT

The system includes a plate with a screw hole and a bone screw wherein the screw and plate cooperate such that the screw is inhibited from back out from the plate after inserted into bone. Described embodiments include a pawl, with and without ratchet, an interfering clip about the screw head, and a snap-fit engagement between the screw and screw hole. The screw hole is preferably provided with openings at at least one of two diametric sides which provide dynamic compression functionality and access under the screw for an instrument to facilitate screw release.

20 Claims, 5 Drawing Sheets

BONE FIXATION SYSTEM AND BONE SCREWS HAVING ANTI-BACK OUT FEATURE

BACKGROUND OF THE INVENTION

1. Field of the Invention

This invention relates broadly to orthopedic devices. More particularly, this invention relates to systems for engaging bone screws relative to bone plates.

2. State of the Art

For various fractures of bones of the body, compressive plating is a well known technique to impart the stabilization desirable for proper healing. In compressive plating, a rigid, typically metal plate is placed on the outer surface of the bone across the fracture, and screws extend through the plate and are secured into the bone on either side of the fracture in a manner which permits the rigid plate to offer support to the bone during healing. The screws include threads along a shaft adapted to engage cortical bone. Most commonly, the head portion of the screw is a standard screw head which provides a compressive force about a corresponding round screw hole of the plate as the fixator is threaded into the bone, thereby causing compression of the plate against the bone.

U.S. Pat. No. Re. 28,841 to Allgower describes a plate that is used with generally standard bone screws having heads with a convex undersurface. The plate includes oblong screw holes which each define at one end an upper ramped portion and a generally smaller radius of curvature about the ramped portion. In use, a hole is drilled into the bone through the screw hole adjacent the ramp and a screw is inserted into the drilled hole and rotated until the head of the screw contacts the ramp. Upon such engagement, there is displacement of the bone plate in a direction to move the ramped portion away from the screw and to cause the plate to apply pressure to maintain the bone parts together about the fracture in tight engagement. The holes in a such a plate are commonly referred to as dynamic compression holes (or DCH). However, micromotion between the bone and the portion of the screw within the bone can cause loosening of the entire assembly, diminishing the stability of the set fracture and a loss of compression across fracture.

More recently, threaded screws with heads which threadably engage in threads in the plate to lock the screws relative to the plate have been used. However, such systems do not provide the necessary control of compression between the plate and bone. Control over compressive forces is lost as soon as the threads of the head of the screw lock relative to the plate. Therefore, such a system provides sub-optimal stability for attachment of certain plates to bone. In addition, even such threaded engagement can loosen over time.

As a result, several systems have used secondary discrete locking elements to lock a bone screw to the plate. For example, U.S. Pat. No. 6,383,186 to Michelson teaches the use of a set screw which seats against the head of the bone screw to prevent backing out of the bone screw. U.S. Pat. No. 6,152,927 to Farris teaches a screw and washer assembly which provides compression against the head of the bone screw to lock the bone screw within the screw hole and prevent it from backing out. Both of these systems require that the surgeon work with separate and small locking elements at the time of the screw insertion, and such small elements may easily become lost in the surgical wound.

U.S. Pat. No. 5,549,612 to Yapp et al. teaches a system in which a screw can be locked relative to the plate with a cam permanently mounted in an aperture in the plate. The cam cannot provide any downward force against the screw head, thereby limiting potential fixation. As such, if the cam rotates just a small amount from a locking angle, the fixation provided by the cam may be lost. Moreover, the shape of the cam (as shown in FIGS. 4 and 4A of the patent) suggests that the cam applies an upward force against the screw head which disadvantageously counters the compressive force of the screw against the plate.

SUMMARY OF THE INVENTION

It is therefore an object of the invention to provide a plate and screw system whereby the amount of compression between the plate and bone can be controlled completely by the surgeon.

It is another object of the invention to provide a plate and screw system which requires the application or activation of no additional elements beyond the insertion of the bone screw to effect an anti-back out feature to the bone screw.

It is also an object of the invention to provide a plate and screw system which is adapted to provide displacement of a plate in a direction which applies pressure to maintain the bone parts together in tight engagement about a fracture.

In accord with these objects, which will be discussed in detail below, a bone plating fixation system includes a plate with one or more screw holes, a bone screw including a head, which in one embodiment includes a substantially circumferential groove with a ring rotatably fixed within the groove. The ring has a small portion, or pawl, extending beyond the circumferential surface of the head. The screw can be rotatably inserted into the screw hole without significant resistance from the pawl as the pawl will deflect into the groove when rotated in the 'insertion' direction. However, the configuration of the pawl creates significant interference that resists the screw head from being rotated in a direction leading to disengagement of the screw from the underlying bone, and the screw can only be disengaged with substantial manual force applied to the screw; i.e., not from the forces of micromotion between the bone and screw shaft. The screw hole may be provided with vertical grooves that function as a ratchet for the pawl of the ring. In addition, the screw hole may be provided with openings at at least one of two diametric sides which provide (i) dynamic compression hole (DCH) functionality from either of two directions and (ii) access under the screw for an instrument to facilitate screw release.

In another embodiment, the pawl is coupled to the plate and the screw head is provided with one or more longitudinal grooves displaced about the circumference. Rotation of the screw head causes the pawl to engage in one of the grooves in a manner which will not be overcome by the forces of micromotion between the bone and screw shaft, but which can be overcome by a surgeon using instrumentation.

In yet another embodiment, both of the screw head and screw hole include circumferential grooves, and one of the screw head and hole include a ring partially provided in the groove. Under compression, the ring can be forced to be substantially completely within the groove of the component to which it is coupled; i.e., the screw head or screw hole. When the screw is inserted into the screw hole, the ring is compressed by the other of the components, and then expands partially into the corresponding groove of the other of the components, thereby providing a snap-fit between the screw and plate.

According to a further embodiment of the invention, the screw hole includes a small lip or tabs about its upper entry which is slightly smaller than the largest diameter across the screw head. When the screw is inserted by the surgeon, it is forcibly inserted past the lip or tabs. The force of micromotion will be insufficient to overcome the interference between the screw head and lip or tabs, and thus the screw head will be trapped within the screw hole. This embodiment is preferred for use with DCH screw holes, as such provide the additional functionality of access under the screw for an instrument to facilitate screw release.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
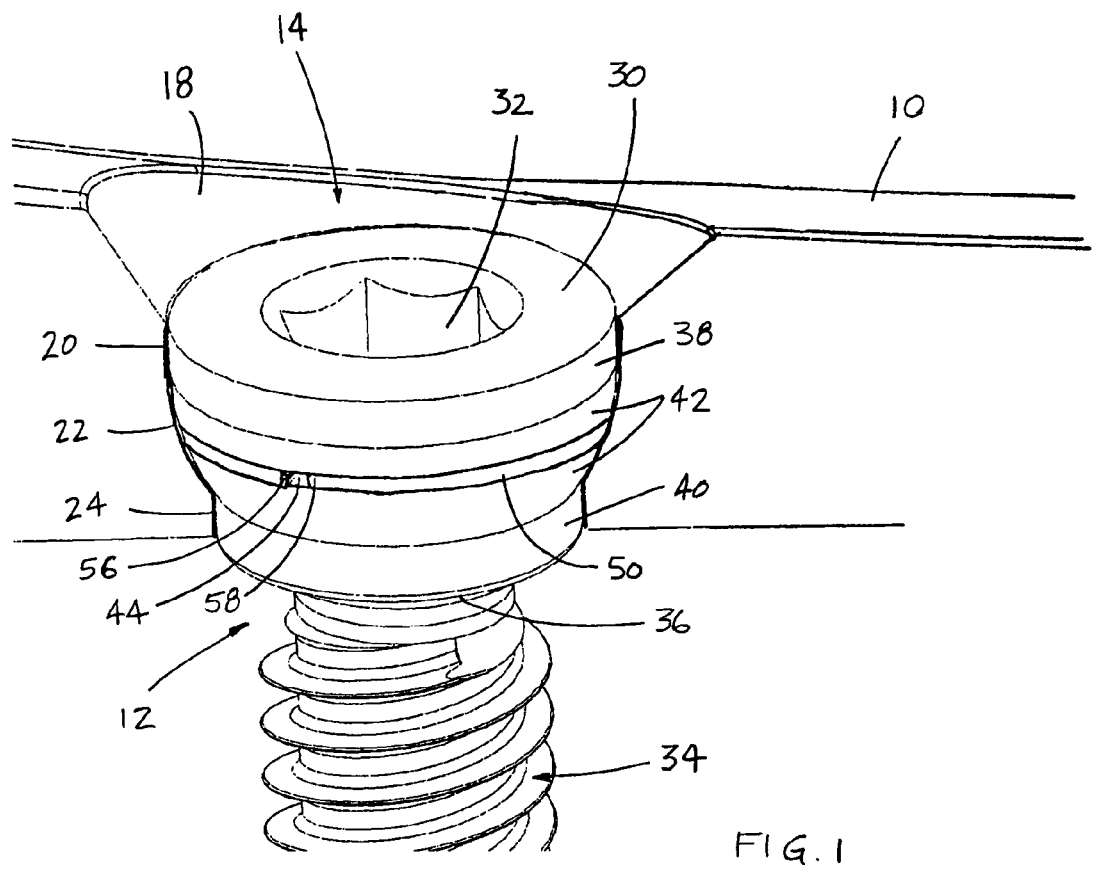
FIG. 1 is a perspective section view of a bone fixation plate provided with a screw having a ring assembled thereto with an anti-back out structure according to a first embodiment of the invention.

Turning now to FIG. 1, an assembly of a bone fixation plate 10 and screw 12 according to the invention is shown. The plate 10 can be any orthopedic plate which has application in providing compression or other stabilization to bone, including but not limited to, plates for fractures of the diaphysis and/or metaphysis of long bones, plates for placement on the mandible or other portions of the skull, and plates for osteosynthesis, particularly along the vertebrae. For example, U.S. Pat. No. 6,706,046 and U.S. Pub. Nos. 20050065524A1 and 20050182405A1, which are hereby incorporated by reference herein in their entireties, describe plates which are suitable for use with the invention. The plate generally includes a plurality of screw holes, one such screw hole 14 shown in FIG. 1. The screw hole 14 is threadless and in a preferred embodiment includes a flared entry 18, an upper larger cylindrical portion 20, a central spherical portion 22, and a lower smaller cylindrical portion 24. The cylindrical portions 20 and 24 alternatively may be frustoconical in shape.

Figure 4:
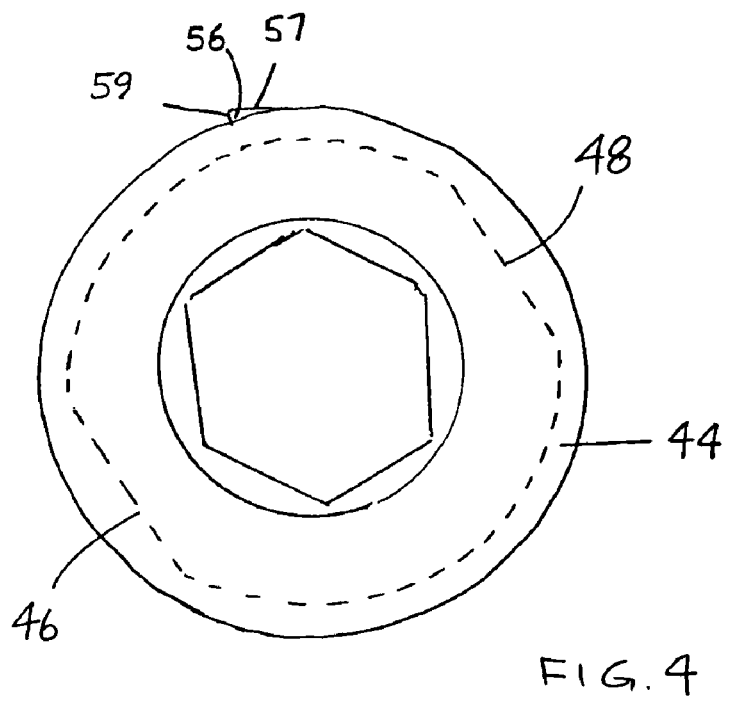
FIG. 4 is a top view of the screw of FIG. 1, indicating the groove for the ring in broken lines.

Referring to FIGS. 1 through 4, the screw 12 includes a head 30 with an upper recess 32, e.g., a hex slot, for a driver, a shaft 34 with bone engaging threads, and a conical taper 36 at the lower end of the head 30 leading into the shaft 34. The head 30 includes upper and lower cylindrical portions 38, 40 and a central spherical portion 42 that matches the dimensions and radius of the bone screw hole 14. The head 30, preferably at the spherical portion 42 includes a circumferential groove 44. The groove 44 preferably includes two diametrically opposed and tangential flats 46, 48 for rotatably fixing a ring 50 within the groove. The ring 50 has a substantially circular outer circumference which corresponds in diameter to the outer diameter of screw head 30 surrounding the groove 44, and two internal flats 52, 54 corresponding to flats 46, 48. The ring 50 also has two ends 56, 58, one of which defines a resilient pawl 56 extending slightly beyond the outer circumference of the screw head 30 at the groove 44 (FIG. 4).

In use, a hole is preferably pre-drilled through the screw hole and into the underlying bone at a location substantially concentric with the circular center defined by the upper and lower cylindrical portions 20, 24 of the bone screw hole 14 (FIG. 1). The head 30 of the screw 12 seats within the space defined by portions 20, 22, 24, and as head 30 is driven toward the bone the plate is compressed against the bone. The bone screw is maintained in a fixed angle (e.g., normal to the lower surface of the plate) by being subject to three points of fixation. The bone screw 12 can be driven until a desired compression is effected. The pawl 56 fixes the level of compression and prevents any loosening that may occur through micromotion. That is, due to the preferred non-radial configuration of the pawl, the screw can be rotatably inserted into the screw hole without significant resistance from the pawl, as the pawl presents a ramped surface 57 and when the screw is rotated clockwise (i.e. in a direction in which the shaft threads are engaged into the bone) the pawl will preferably at least partially deflect into the groove 44. At most, the pawl will tap a shallow thread into the screw hole. However, the configuration of the pawl 56 defines a sharp 59 which creates significant interference with the walls of the screw hole when the screw is attempted to be rotated counter-clockwise; i.e., in a direction in which the shaft threads are disengaged from the bone. As such, the pawl 56 resists unintentional backing out by the screw from the screw hole and such resistance can only be overcome with substantial and intentional manual force applied to the screw, and not from the micromotion between the bone and the screw shaft.

Figure 5:
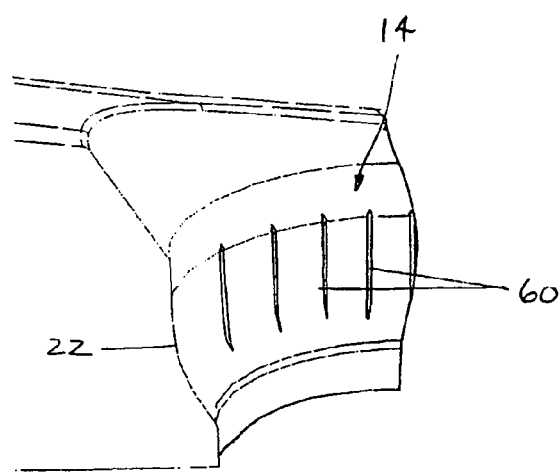
FIG. 5 is a perspective broken section view of the plate of FIG. 1.
Figure 2:
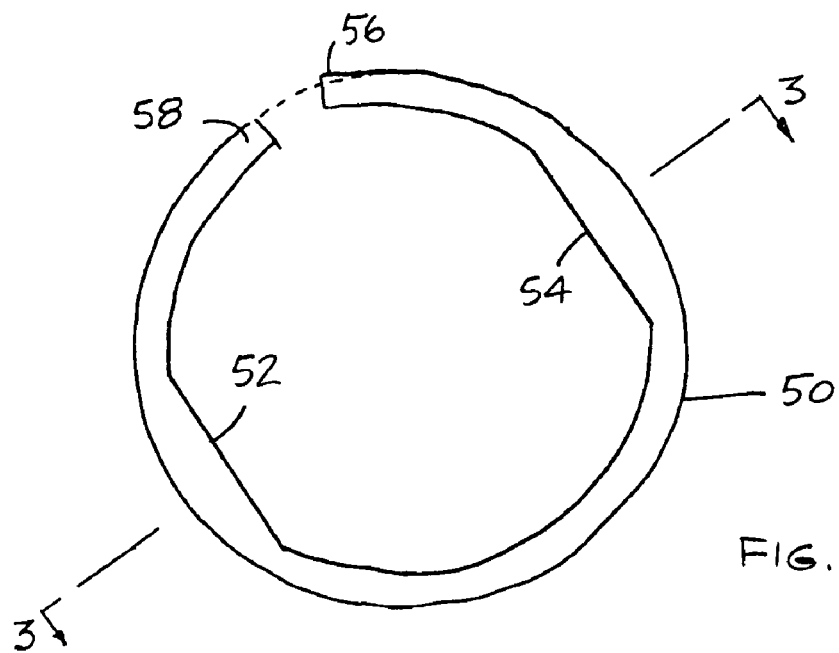
FIG. 2 is a plan view of the ring of FIG. 1.
Figure 3:
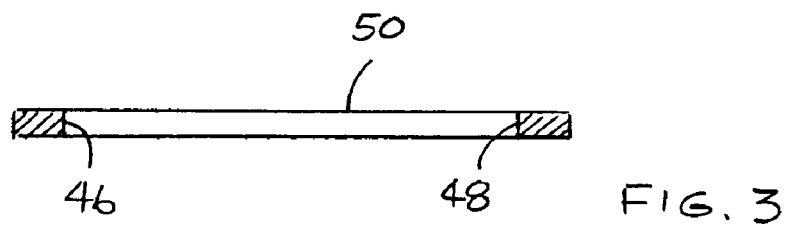
FIG. 3 is a section view across line 3-3 in FIG. 2.

Turning now to FIG. 5, the screw hole 14 may be provided with one or more vertical grooves 60, particularly in the spherically curved portion 22, that function as a ratchet for the pawl 56 of the ring 50 (FIG. 2). Such structure provides a positive feedback for the surgeon to indicate advances of the screw. The grooves 60 can be located at a specific angular displacement about the circumference, e.g., spaced 20° apart, which depending upon the pitch of the shaft thread will correspond to a specific longitudinal advancement of the thread into bone and/or incremental compressive force between the plate and bone.

Figure 6:
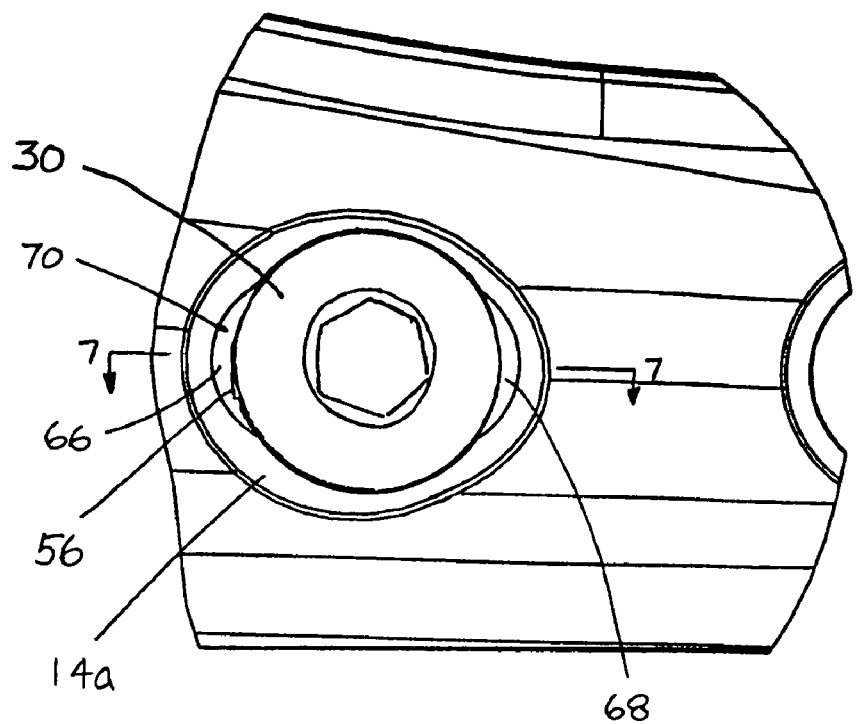
FIG. 6 is a top view of a bone fixation plate, wherein the screw holes provides dynamic compression from either of two directions and two access locations to facilitate removal of the screw.
Figure 7:
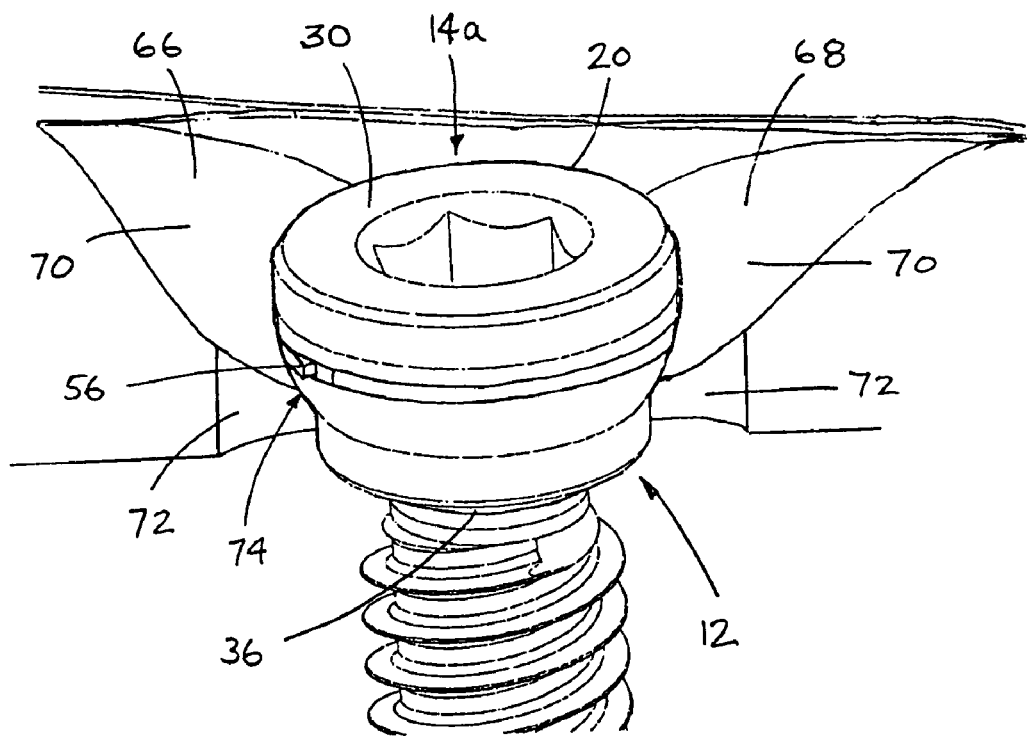
FIG. 7 is a perspective section view across line 7-7 in FIG. 6.

In addition, referring to FIGS. 6 and 7, the screw hole 14a may be similar to hole 14 but provided with openings 66, 68 at at least one of two diametric sides which provide (i) DCH functionality from either of two directions and (ii) access under the screw head 30 for an instrument to facilitate screw release after a screw is seated in the screw hole. More particularly, the openings 66, 68 at the diametric sides are defined by a portion of the screw hole having an upper ramped surface 70 and a lower smaller radius of curvature 72 than the lower cylindrical portion 24 (FIG. 1). Much like the dynamic compression screw hole described in U.S. Pat. No. Re. 28,841 to Allgower, which is hereby incorporated by reference in its entirety herein, such a screw hole allows the screw to apply force against either upper ramped surface 70 to drive the plate in a direction transverse the axis of the screw. By providing ramped surfaces 70 at diametric locations about the screw hole, the plate may be driven in either of two directions depending upon screw placement.

In accord with another mode of using the plate and the screw 12, a hole is drilled for the screw 12 along an axis normal to the plate which is offset towards one of the ramped surfaces 70 and generally concentric with one of the curves 72; i.e., away from the circular center defined by the upper and lower cylindrical portions 20, 24 (FIG. 1) of the screw hole 14a. The bone screw 12 is then driven into the hole until the lower conical surface 36 the screw head contacts the ramp 70 and thus causes displacement of the plate 10 by the distance required to seat the head 30 in the central concave spherical portion 22 (FIG. 1). This displacement applies pressure which maintains bone parts together about a fracture in tight engagement. The screw 12 is tightened, with the pawl 56 located to engage the central portion of the hole and resist rotation in an opposite disengaging direction.

In addition, if screw removal is necessary, the screw may be rotated (generally by no more than 90°) to position the pawl 56 within an opening 66, 68 to disengage the pawl from the screw and facilitate screw removal. Moreover, the opening 66, 68 provides sufficient access for a relatively flat tipped instrument to be positioned against the undersurface of the screw head, e.g., at 74, to pry up the screw head if screw removal is necessary.

Figure 8:
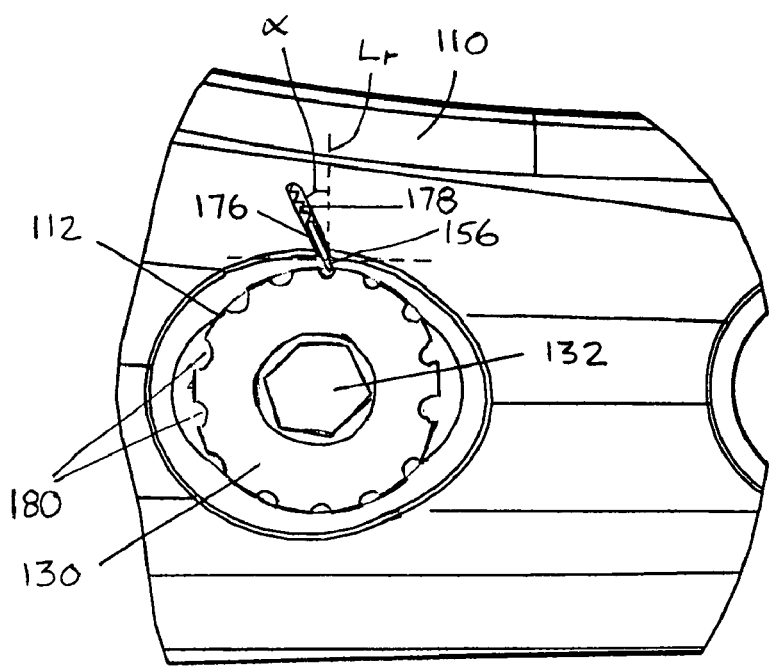
FIG. 8 is a top view of a second embodiment of an anti-back out screw assembly.

Turning now to FIG. 8, another embodiment of the invention is shown. The pawl 156 is coupled to the plate 110. The pawl 156 is fixed at least partially within a slot 176, and may be spring-biased on spring 178 to move longitudinally within the slot. The screw 112 includes a screw head 130 provided with one or more longitudinal ratchet grooves 180 displaced about its circumference. Rotation of the screw head 130 causes the pawl 156 to engage in one of the grooves 180 in a manner which will not be overcome by the forces of micromotion, but which can be overcome by a surgeon using a driver inserted into the driver opening 132 of the screw 112. Alternatively, the pawl may be retracted against the spring-bias to eliminate impediment to screw removal (as well as initial screw insertion). In addition, the pawl 156 may be oriented at an angle α relative to a radius $L_T$ to the screw hole to facilitate screw insertion, but to inhibit screw back out.

Figure 9:
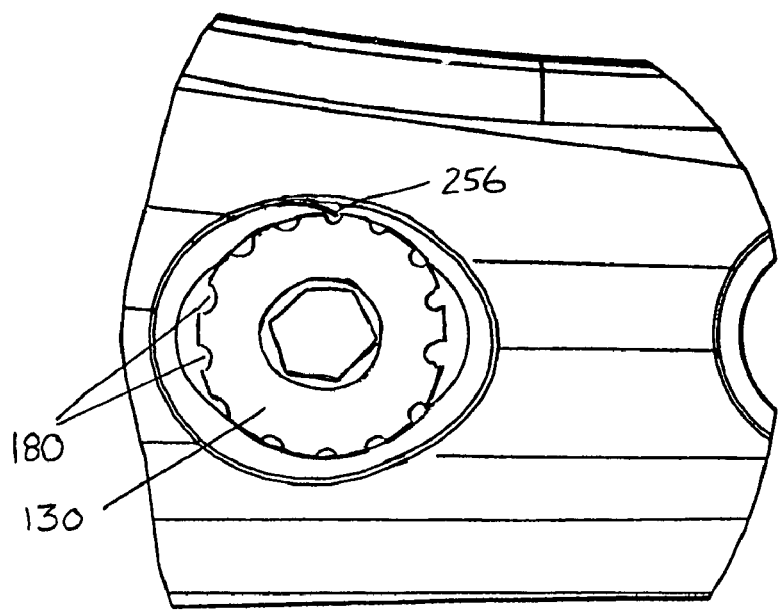
FIG. 9 is a top view of a third embodiment of an anti-back out screw assembly.

Referring to FIG. 9, another embodiment of the invention is shown. The pawl is a is resilient spring steel member 256 which enters the screw hole and may enter grooves 180 in the screw head 130, but which is easily deflected when the screw head 130 is rotated in a direction of a screw insertion, but which resists screw rotation in disengagement direction.

Figure 10:
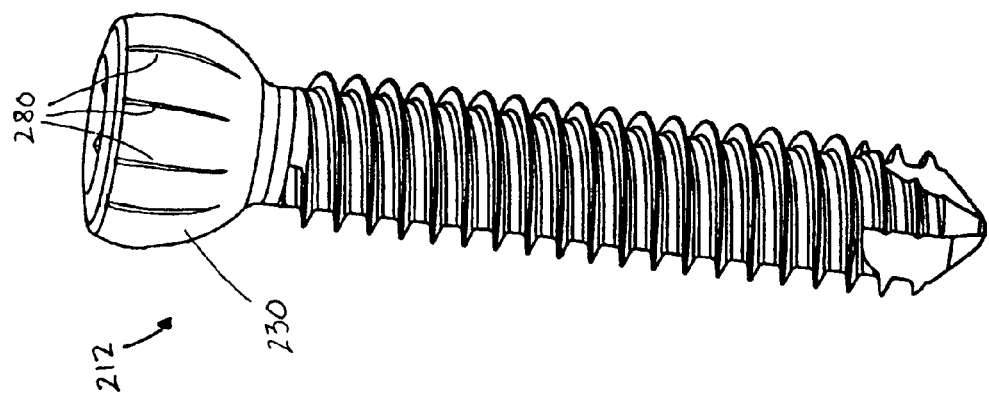
FIG. 10 is a perspective view of a variable angle screw according to the invention.

Turning to FIG. 10, the embodiments shown in FIGS. 8 and 9 may also be used with a variable angle screw 212 having a substantially completely spherically curved screw head 230. Such a screw head 230 is preferably provided with one or more longitudinal grooves 280 for engagement with a pawl or similar member. The grooves may be curved along meridians of the screw head.

Figure 11:
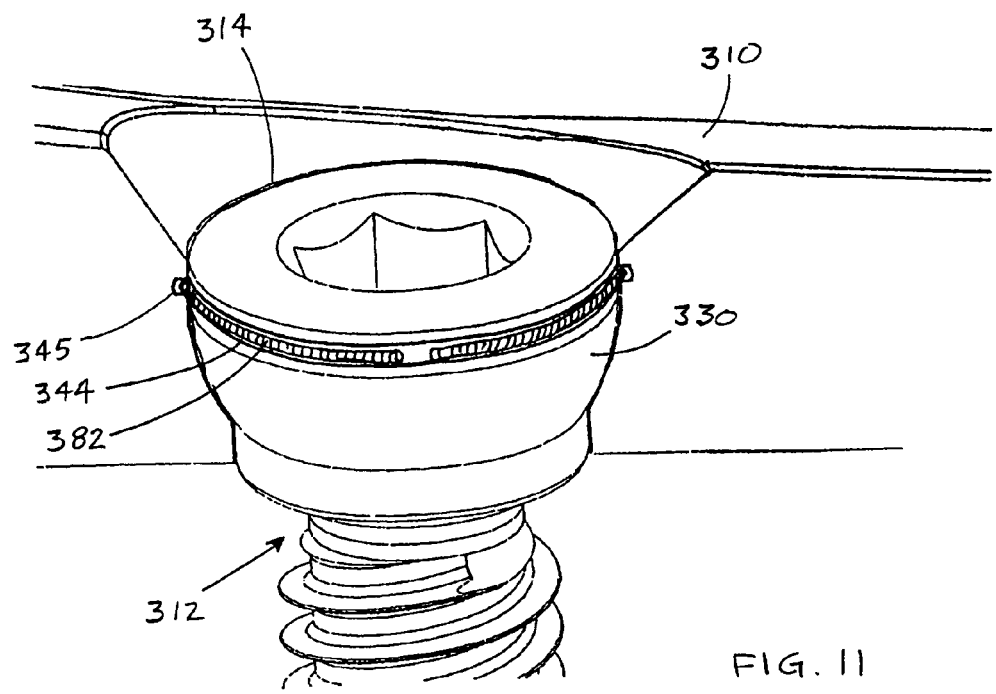
FIG. 11 is a perspective section view of a fourth embodiment of an anti-back out screw assembly.

Turning now to FIG. 11, another embodiment is provided in which both the screw head 330 and the screw hole 314 include circumferential grooves 344, 345. A resilient C-ring 382 is substantially provided in the groove 344 on the screw head 330 but is expanded slightly beyond the circumferential surface of the screw head. When the screw is driven into the screw hole 314, the groove is sufficiently deep to permit the ring 382 to be substantially completely compressed within the groove 344 of the screw head. Once the screw 312 is driven so that the screw head and screw hole grooves 344, 345 meet, the ring 382 expands outward into the groove 345 of the screw hole, thereby providing a snap fit engagement between the screw 312 and plate 310. The C-ring may alternatively be an O-ring. As yet another alternative, the ring may be initially fixed within the groove 345 of the screw hole, and then enter the groove 344 on the screw head when the screw head is seated in the screw hole. As described above, the screw hole may also include access openings to facilitate screw removal.

It is appreciated that the general shape of the screw hole in any of the embodiments described above permits the use of variable angle screws having spherically curved heads matching the curvature of the central spherical portion. Such screws would be able to be directed at any surgeon directed angle within a range of angles. In addition, such screws may also be provided with a pawl, grooves, or rings, as described above to prevent screw back out.

There have been described and illustrated herein embodiments of bone fixation systems and bone screws. While particular embodiments of the invention have been described, it is not intended that the invention be limited thereto, as it is intended that the invention be as broad in scope as the art will allow and that the specification be read likewise. It will therefore be appreciated by those skilled in the art that screw holes and screws of other shapes and designs, while still provided with the features of the invention, are within the scope of the invention. Other modifications can be made to the provided invention without deviating from its scope as claimed.

What is claimed is:

1. A bone fixation system, comprising:
   a) a bone plate including a dynamic compression bone screw hole;
   b) a bone screw having
      a non-threaded head portion having a upper surface, a lower surface, a peripheral surface extending therebetween, and a circumferential groove extending about the peripheral surface, and
      a shaft portion provided with bone-engaging threads extending from said head portion; and
   c) a split ring discrete from said bone screw, said ring substantially completely recessed in said groove and rotationally fixed relative to said bone screw, said ring having first and second ends, said ring recessed such that only said first end extends out of said groove so as to contact said bone plate surrounding said bone screw hole and provide rotational resistance when said bone screw is rotated in a direction of disengagement from bone,
      wherein said bone screw hole includes at least one access opening extending from an upper portion of said plate to a lower portion of said head portion of said screw when said head portion of said screw is seated in said bone screw hole.

2. A bone fixation system according to claim 1, wherein: said head portion includes an upper cylindrical portion, a lower cylindrical portion, and a central spherically curved portion.

3. A bone fixation system according to claim 2, wherein: said groove is provided in said central spherically curved portion.

4. A bone fixation system according to claim 1, wherein: said groove includes at least one tangential flat.

5. A bone fixation system according to claim 4, wherein: said groove includes exactly two diametrically opposed tangential flats.

6. A bone fixation system according to claim 5, wherein: said ring has two internal flats corresponding to said flats of said groove.

7. A bone fixation system according to claim 1, wherein: said first end is spaced apart from a radially internal surface of said groove, and said first end is resiliently deformable into said groove when said screw is rotated said bone screw is rotated in a direction of engagement into bone.

8. A bone fixation system according to claim 1, wherein:
said rotational resistance can be overcome by the application of manual force to rotate said bone screw in a direction of disengagement from bone.

9. A bone fixation system according to claim 1, wherein:
said bone fixation hole includes exactly two access openings from an upper portion of said plate to a lower portion of said head portion of said screw when said head portion of said screw is seated in said bone screw hole, said access openings located at diametrically opposite sides of said fixation hole.

10. A bone fixation system, comprising:
a) a bone plate including a non-threaded dynamic compression screw hole;
b) a bone screw having a non-threaded head portion and a shaft portion with bone-engaging threads, said head portion including a circumferential groove; and
c) an element rotationally fixed relative to said bone screw in said groove and in contact with said bone plate so as to inhibit said bone screw from backing out of said screw hole, but not prevent said bone screw from being rotatably removed from said plate by manual application of a force to said screw in a rotational direction of disengagement from bone, said element completely recessed in said groove except for a point of contact with said bone plate,
wherein said bone screw hole includes at least one access opening extending from an upper portion of said plate to a lower portion of said head portion of said screw when said head portion of said screw is seated in said bone screw hole.

11. A bone fixation system according to claim 10, wherein:
said bone fixation hole includes exactly two access openings from an upper portion of said plate to a lower portion of said head portion of said screw when said head portion of said screw is seated in said bone screw hole, said access openings located at diametrically opposite sides of said fixation hole.

12. A bone fixation system, comprising:
a) a bone plate including a bone screw hole; and
b) a bone screw having a non-threaded head portion and a shaft portion with bone-engaging threads, said head portion including an upper cylindrical portion, a lower cylindrical portion, and a spherically curved central portion between said upper and lower portions, said central portion including a circumferential groove; and
c) a split ring discrete from said head portion and rotationally fixed within said circumferential groove, said split ring having first and second ends, wherein said split ring is recessed in said groove and only said first end extends out of said groove, said first end defining a pawl that contacts said bone plate surrounding said bone screw hole which provides rotational resistance when said bone screw is rotated in a direction of disengagement from bone.

13. A bone fixation system according to claim 12, wherein:
said first end of said split ring defines a resilient non-radially oriented pawl, wherein,
when a first rotational force is applied to said screw head to rotate said screw head within said screw hole in first rotational direction, said pawl at least partially recesses into said groove of said head portion of said screw to permit said rotation in said first rotational direction, and
when an opposite second rotational force is applied to said screw head to rotate said screw head within said screw hole in an opposite second rotational direction, said pawl inhibits rotation of said screw head within said screw hole.

14. A bone fixation system according to claim 12, wherein:
said groove includes at least one tangential flat, and said ring has at least one internal flats corresponding to said at least one flat of said groove.

15. A bone fixation system according to claim 12, wherein:
said groove includes exactly two diametrically opposed tangential flats, and said ring has exactly two internal flats corresponding to said flats of said groove.

16. A bone fixation system, comprising:
a) a bone plate including an elongate bone screw hole;
b) a bone screw having
a non-threaded head portion having a upper surface, a lower surface, a peripheral surface extending therebetween, and a circumferential groove extending about the peripheral surface, and
a shaft portion provided with bone-engaging threads extending from said head portion; and
c) a split ring discrete from said bone screw, said ring rotationally fixed relative to said bone screw, said ring having first and second ends, wherein said ring is substantially completely recessed in said groove such that only said first end extends out of said groove so as to contact said bone plate surrounding said bone screw hole and provide rotational resistance when said bone screw is rotated in a direction of disengagement from bone.

17. A bone fixation system according to claim 16, wherein:
said bone screw hole includes first and second access openings from an upper portion of said plate to a lower portion of said head portion of said screw when said head portion of said screw is seated in said bone screw hole, said first and second access openings located at diametrically opposite sides of said head portion of said screw.

18. A bone fixation system according to claim 17, wherein:
said first and second access openings extend completely through said plate.

19. A bone fixation system according to claim 16, wherein:
said head portion includes an upper cylindrical portion, a lower cylindrical portion, and a central spherically curved portion.

20. A bone fixation system according to claim 16, wherein:
said groove includes exactly two diametrically opposed tangential flats, and
said ring has two internal flats corresponding to said flats of said groove.

* * * * *